(12) United States Patent
Garcia-Aparicio

(10) Patent No.: US 8,195,320 B2
(45) Date of Patent: Jun. 5, 2012

(54) METHOD FOR MANUFACTURING DIGITALLY-DESIGNED REMOVABLE DENTAL PROSTHESES AND SYSTEM REQUIRED FOR THIS PURPOSE

(76) Inventor: Juan Carlos Garcia-Aparicio, Benidorm (ES)

( * ) Notice: Subject to any disclaimer, the term of this patent is extended or adjusted under 35 U.S.C. 154(b) by 796 days.

(21) Appl. No.: 12/281,952

(22) PCT Filed: Mar. 8, 2007

(86) PCT No.: PCT/ES2007/000123
§ 371 (c)(1),
(2), (4) Date: Sep. 5, 2008

(87) PCT Pub. No.: WO2007/101898
PCT Pub. Date: Sep. 13, 2007

(65) Prior Publication Data
US 2009/0075237 A1   Mar. 19, 2009

(30) Foreign Application Priority Data
Mar. 8, 2006   (ES) .................................. 200600572

(51) Int. Cl.
*G06F 19/00* (2006.01)
*A61C 13/08* (2006.01)
(52) U.S. Cl. ...... 700/97; 700/98; 433/201.1; 433/202.1; 433/213; 433/215
(58) Field of Classification Search ............ 700/97, 700/98; 433/201.1, 202.1, 213, 215
See application file for complete search history.

(56) References Cited

U.S. PATENT DOCUMENTS

| | | | |
|---|---|---|---|
| 6,488,503 B1 * | 12/2002 | Lichkus et al. ............ 433/202.1 |
| 6,619,959 B2 * | 9/2003 | Iiyama et al. .................. 433/215 |
| 6,648,640 B2 * | 11/2003 | Rubbert et al. .................. 433/24 |
| 6,835,066 B2 * | 12/2004 | Iiyama et al. .................. 433/223 |
| 6,970,760 B2 * | 11/2005 | Wolf et al. ..................... 700/163 |
| 7,153,135 B1 * | 12/2006 | Thomas ........................ 433/213 |
| 7,236,842 B2 * | 6/2007 | Kopelman et al. .............. 700/98 |
| 7,762,814 B2 * | 7/2010 | van der Zel ................ 433/201.1 |
| 2005/0023710 A1 | 2/2005 | Brodkin et al. |
| 2009/0042167 A1 * | 2/2009 | Van Der Zel ................ 433/215 |
| 2009/0075237 A1 * | 3/2009 | Garcia-Aparicio ........ 433/202.1 |

FOREIGN PATENT DOCUMENTS

| WO | WO 2005/004743 A1 | 1/2005 |
|---|---|---|
| WO | WO 2006/005284 A2 | 1/2006 |

* cited by examiner

*Primary Examiner* — Michael D Masinick
(74) *Attorney, Agent, or Firm* — Albert Bordas, P.A.

(57) ABSTRACT

The system, object of the invention consists of a unit for scanning a mould produced from the sample from a patient's mouth, an image which is sent to digital generation equipment of a removable dental prosthesis, producing a file that is transmitted to metal piece manufacturing equipment by means of sintered powder applying a high-energy ray. The design stages consist of the relief of the mould, the calculation of the insertion axis, the paralleling of the teeth, designing of the elements or components of the prosthesis such as lattice, clamp, stop, major connector, minor connector, bristle, pearls, lingual bars, extrusion of the different elements designed, smoothing of the sharp edges, elimination of the superpositions of the different elements designed and conversion of a closed continuous connected surface to a three-dimensional one.

17 Claims, 8 Drawing Sheets

METHOD FOR MANUFACTURING DIGITALLY-DESIGNED REMOVABLE DENTAL PROSTHESES AND SYSTEM REQUIRED FOR THIS PURPOSE

OBJECT OF THE INVENTION

Objects of this invention are both the manufacturing process of digitally designed removable dental prostheses and the means necessary to perform said process, that is to say is it makes reference to both the technical characteristics used in the design stages for the digital generation of removable dental prostheses and all the material means used to manufacture or produce removable dental prostheses.

This invention is characterized in that it uses equipment to manufacture pieces by means of a successive application of metal powder layers, which are then bonded together, by means of the accurate application of a laser beam, from the information contained in an electronic file which has the final configuration of the prosthesis one wants to produce, which allows the automatic manufacturing of removable dental prostheses from computer-generated design.

This system is composed of equipment to scan the mould produced after the impression made of the patient's mouth, computerized means which are used to make the design of the removable prosthesis virtually, in such way that a file is produced containing the information of the final desired configuration of the prosthesis. This file is transmitted to manufacturing equipment).

Therefore, this invention is included within the area of systems and means used to manufacture dental pieces using manufacturing equipment by means of sintered powder compacted by the application of a laser beam.

BACKGROUND OF THE INVENTION

To date, the automatic manufacturing of dental pieces from a digital file is well known, as is disclosed in the patent US 2004/0106087, which describes a method used for the manufacturing of dental prostheses by the restoration of ceramic dental pieces, using laser equipment controlled by a computer in charge of giving form to a dental piece by removal of the material from the original ceramic block, until the dental piece is produced with the form desired.

Although this system automates the production of dental pieces, it has several drawbacks and limitations. On the one hand, the quantity of waste material is quite high, possibly even exceeding 67% in practice; on the another hand, the time taken to produce one dental piece is quite long in comparison with what would be desirable to achieve in the industry and finally, the most important limitation is that this system cannot produce removable dental prostheses, because they have a configuration and geometry which makes it impossible to produce a prosthesis by removing material from an initial block.

The manufacturing process of removable dental prostheses is currently completely manual and the final result depends on many determining factors such as the proficiency and accuracy of the dental technician, the casting process using the centrifugal machine, which is not always perfect. It is undoubtedly a craft process not free form difficulties and eventualities, which requires a large amount of manpower.

On the another hand, there are patents such as WO 20055080029 which discloses a process to manufacture metal products by sintering metal powder layers by applying high-energy rays, specifically laser beams or electron beams.

This invention mentions the possibility of producing dental pieces such as crowns or bridges. But, at no time does it mention the process or specific stages necessary to manufacture a removable prosthesis with equipment similar to that described. In other words, it does not specify how the digital generation of a removable prosthesis would be carried out with its unavoidable technical difficulties, which could be used by the above mentioned equipment. It is very important to underline the fact that the prostheses, which will be manufactured, are removable, since, on the one hand, there are no means of digital generation of dental prosthesis and the machines do not have sufficient accuracy to achieve the described geometry.

Therefore, an object of the present invention is to develop the required process for the digital generation of removable prostheses, as well as the system necessary for the manufacturing of said prostheses with the claimed process.

DESCRIPTION OF THE INVENTION

The object of the invention is a manufacturing process of digitally designed removable prostheses and the system necessary in order to perform said process. In other words, the means that would be necessary for the automatic production of removable dental prostheses, as well as the digital generation stages of a removable prosthesis, where it specifies in said stages the exact technical characteristics which will allow the virtual construction of a removable prosthesis using digital means.

The system is basically composed of three elements: equipment to scan the mould of a patient's mouth; whereby a file is produced which will be sent to equipment or a computer wherein the design or digital generation of the removable prosthesis will be carried out. Once the desired digital prosthesis is finished and produced, the file, which contains all the exact information, is sent to generation equipment, manufacturing dental pieces, which are manufactured by sintered powder using a laser beam.

The file sent to the generation/manufacturing equipment/machine of dental prosthesis contains the information regarding a closed, continuous connected surface.

The three-dimensional representation of the digitized mould is formed by a series of adjacent triangles, where each of the triangles is defined by its vertices, and them by co-ordinates (x, y, z); each one of the vertices also has associated a normal, which is the mean of the normal of the surfaces of the adjacent triangles.

The design and digital generation process of the removable dental prosthesis, after the reception of the file containing the three-dimensional digitized mould, starts with an optional stage of digital relief, from the original model, which would be done only in the case that it had a lattice and just in the area where the lattice would be placed.

Once the relief piece is produced, if wanted, the insertion axis is calculated, also digitally. To perform this operation we look for the plane, which intersects or cuts with the greatest number of dental pieces on the same level, a process, which will give us an insertion angle, which is saved. The insertion axis can be modified by the user.

After the calculation of the insertion axis the digital paralleling is performed of the teeth, which require it, for example the teeth whereon the clamps, will be placed. These calculations will be done by selecting the tooth or dental piece to be paralleled.

Paralleling seeks the perimeter line of the dental piece whereon we obtain sufficient retention of the clamp; therefore, the display of the retentive areas is allowed on the digitized mould.

To ascertain the degree of retention of each area, it indicates the angle formed by the normal of the tangent plane of the marked point of each dental piece with the insertion axis.

Thus, when the angle formed by the normal of the tangent plane to be paralleled with the insertion axis is 90°, the retention is minimal, whilst if it was 0°, the retention is maximal.

The retention is marked using a colour scale or any other indicator means.

Having selected the point to be paralleled and ascertained the possible degree of retention, the programme proceeds to perform a relief or elevation of the digitized mould until leaving the digitized mould's surface at 90° in relation to the selected point of the dental piece.

A point where the angle of the normal of the tangent plane thereto forms a 90° angle with the insertion axis would form part of the equator line, for which purpose the user will decide up to which point under the equator line he/she wants to parallel, that is to say to elevate the digitized mould.

Once the paralleling has been performed, that is to say is the perimeter line of the dental piece offering sufficient retention of the clamp or similar, has been produced, we will continue with the next stages.

Having performed the previous steps we can start designing the different components of the prosthesis on the model, the possible components of the prosthesis which can be used being: major connector minor connector, stop, lattice, clamp, lingual bar, bristle and pearls.

Both the lattice and the clamp can be assigned from a range of initial casts, it being possible to assign a different thickness.

Finally, a preliminary view of the prosthesis can be made once the mould is removed, observing any possible deficiencies that could occur.

The designing process of the different elements or components, which form the removable prosthesis, is performed on the computer screen, having the three-dimensional representation of the digitized mould as a base.

The profile or shape of the lattice and connectors is generated on the three-dimensional representation of the digitized mould.

Before starting to make the profile of the lattice and connector surface, their thickness will be chosen, as well as the web or design of the lattice, chosen from a library.

With regard to the clamps, the profile or run which they must adopt or follow is designed, a design which is made on the three-dimensional representation of the digitized model. In relation to the design of the clamps, we can chose from a library the section of the clamp and the form to be adopted by them, both initial and final.

Additionally, with regard to the lingual bar, the run of the lingual bar will be marked, it being possible to choose both its section and shape from a library.

Therefore, all the elements of the removable prosthesis are basically formed by a succession of points defined by their three spatial co-ordinates, in addition to the chosen parameters such as the section, the final shape of the clamp, the initial shape, web of the lattice, etc.

When the basic form of the elements, which form the removable prosthesis, is defined, we must proceed to the extrusion thereof i.e. to give them volume.

The process is different for clamps, lingual bars, than for lattices or connectors.

For clamps or lingual bars, the extrusion process consists of the following stages:

The definition of the flat part of the clamp or lingual bar, defined according to the profile or run, marked on the digitized model; for this purpose, we define an upper and a lower band in relation to said profile or run. These upper bands are defined automatically according to the section of the chosen clamp. A library was previously created which associates the types of clamps with the upper and lower bands, which must be marked on the profile or run of the clamp.

The extrusion for each point of the profile or run of the clamp; for this purpose, the corresponding section is associated to each point of the profile or run according to the chosen clamp.

Therefore, a succession of sections is finally generated, arranged in a continuous way, which form the clamp with its definitive form.

For lattices or connectors, the extrusion process is as explained below. The lattice or connector will be defined by a closed profile or contour formed by a succession of points which are defined by their three co-ordinates. Each one of the points of the closed profile or contour of the lattice or connector will be marked inside a triangle of those, which form the digitized model.

The mean of the normal of the triangles, which contain the points of the profile or contour of the lattice or connector, is found; this way we get an approximate projection direction.

Next, all the triangles which form the digitalized mould is projected on a plane whose normal is the mean of the normal previously obtained, going from three co-ordinates (x, y, z) to two co-ordinates (p', v').

Likewise, the points which forms the profile or contour of the lattice or connector are projected on said plane whose normal is the mean of the normal the triangle contain, which contain the points of the profile or contour.

Said points are joined by a polygon, which forms the profile or contour of the lattice or connector, ascertaining which of the projected triangles will be outside or inside said shape.

We then examine all the memory where we stored the data in relation to the co-ordinates (p, v) of the projected triangles to ascertain:
- the triangles of the mould, which are inside the traced polygon, i.e. those, which have the three vertices inside the polygon
- the triangles, which have one of the vertices inside the traced polygon
- the triangles, which have two of their vertices inside the polygon
- the triangles which, even having the three vertices outside the traced polygon, are cut by said polygon In the first case, the triangles, which have all their vertices inside the traced polygon, which correspond to the design, which we want to give to the piece, are marked directly, recovering their values before the projection.

In the case of the triangles which have one of their vertices inside the marked polygon, the cutting points of the polygon are found with the side lines of the triangle and it is ascertained if there are or are not any points within said triangle, performing a triangulation process of the part of the triangles cut by the polygon.

If the triangles have two of their vertices inside the marked polygon the cutting points are found and it is ascertained if there is any point of the polygon contained in said triangle, also performing a triangulation process of the surface cut by the triangles.

In the last case to ascertain those triangles, which have no vertices inside the spaced defined by the defined polygon.

All the triangles, which form the digitized mould are defined by their vertices and each one thereof by their three co-ordinates, as well as by a normal, which is the mean of the normal of the surfaces of the adjacent triangles.

In the newly obtained triangles which form part of the interior of the polygon as they have one or two of their vertices inside the polygon or have part of its surface without any vertex inside the polygon, the three-dimensional data is recovered from the known data, whilst the newly obtained vertices, which are basically the cutting points with the polygon and have co-ordinates (p', v') are transformed to their three-dimensional co-ordinates (x, y, z), taking in consideration the projection made according to the normal obtained.

In other words, a closed profile or contour is finally obtained, formed by triangles, all interior, and they are defined by their vertices and them by their three-dimensional co-ordinates.

Next, since the total projection of the digitalized model has been made, we do the following:

Identify the surfaces, which share at least one edge.

Choose the surface of interest, which will be the surface, which is closer to the defined profile or contour.

Extrude or elevate all the points of the selected surface in the normal direction of each point.

Next, a Gauss filter is used, which smoothes the sharp edges, applying it on all surfaces, except those, which are in contact with the palate.

Next, the file should be prepared for its manufacturing, and the following should be done:

Join the different elements, which form the designed removable prosthesis eliminating the existent superpositions between the pieces. This process is known as voxelization.

Finally, a conversion process is performed of a compact volume to a 3D closed continuous connected surface.

If necessary, smoothing filters can be applied.

DESCRIPTION OF THE FIGURES

To complement the description, which will be made, and in order to help towards a better understanding of its characteristics, the present specification is accompanied by a set of plans whose figures, illustratively but not limitatively, represent the most significant details of the invention.

PREFERRED EMBODIMENT OF THE INVENTION

In light of the figures, a preferred embodiment of the proposed invention is described below.

As we have previously indicated, the system for the manufacturing of removable dental prostheses, which have been digitally generated, consists of a scanner, means of computation or computer for the design and digital generation of a removable prosthesis, and manufacturing equipment of metal pieces from a file, using in the manufacturing sintered powder whereon a high-energy ray will be applied.

Figure 1:
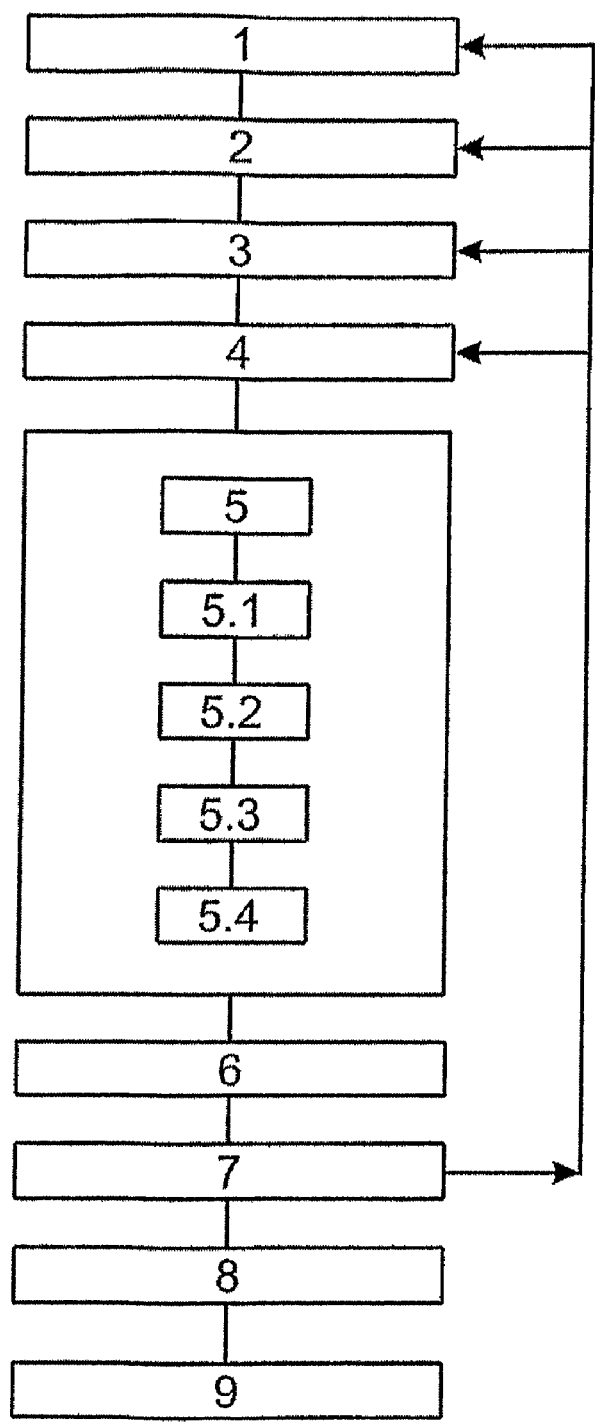
FIG. 1 shows the stages, which form the generation process of the removable dental prostheses digitally.

The generation process of a removable dental prosthesis, as indicated in FIG. 1, starts with the scanning (1) of the mould of the patient's mouth; the process continues with the transmission (2) of the file produced to the means of computation or computer; it then continues with the stages of digital generation of the removable dental prosthesis.

The digital generation of the removable dental prosthesis consists of the following stages:

digital relief (3) of the transmitted mould, in the area where a lattice is disposed, if placed digital calculation (4) of the insertion axis Digital paralleling of (5) the teeth, which require it Disposal and digital design (6) of the different elements and components, which the removable prosthesis requires. Among the objects used will be: lattice, clamp, major connector, minor connector, stop, bristle, pearl, lingual bar.

The design of the different components of the removable dental prosthesis is performed on the three-dimensional image of the digitized mould. We can choose from the options of a library to have the different configurations the elements of the prosthesis may have.

In turn, the paralleling stage (5) of the dental pieces that so require consists of the following sub-stages:

Display of the different retention areas (5.1)

Production of the minimal retention area (5.2) or equator of the selected piece selection (5.3) of the paralleling line underneath the dental equator line elevation (5.4) of the surface of the digitized mould to the paralleling line Having completed the disposal of the different elements, the process continues with the following actions:

Modifications (7) of any of the previous stages

Preliminary view (8)

Saving (9) of the final file

Figure 2:
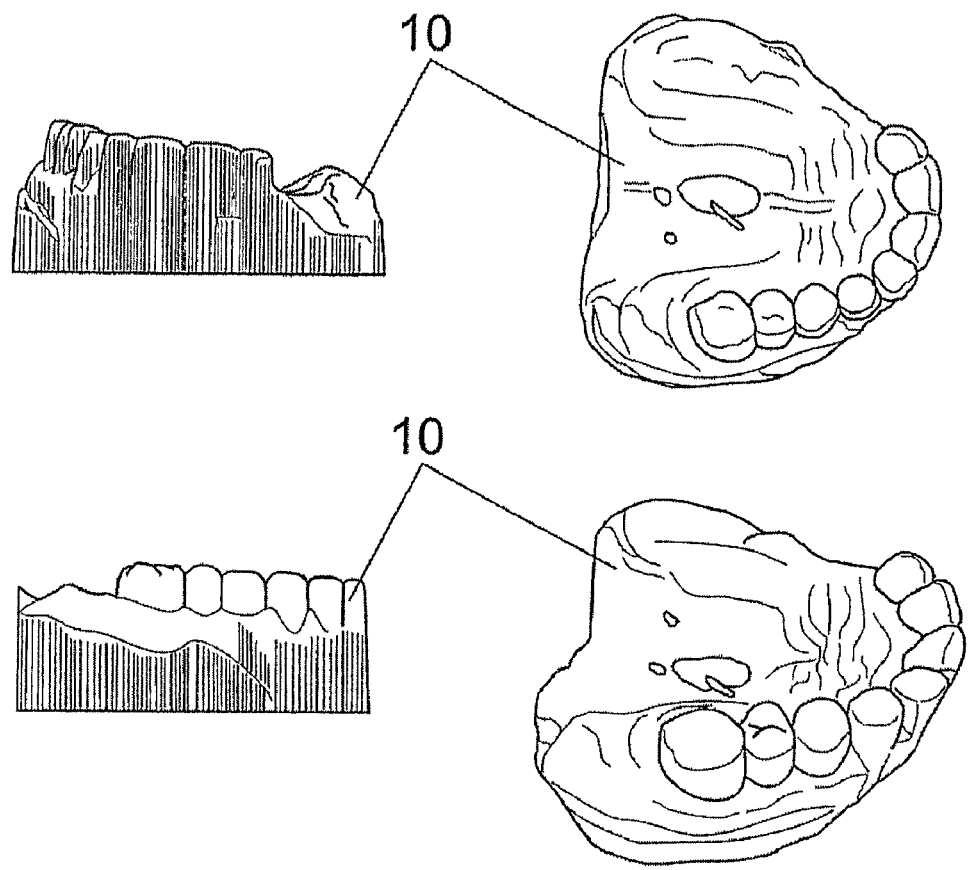
FIG. 2 shows a representation, formed by a front view, a left side view, a plan view and a perspective view of the digitized mould on which we will work.
Figure 6:
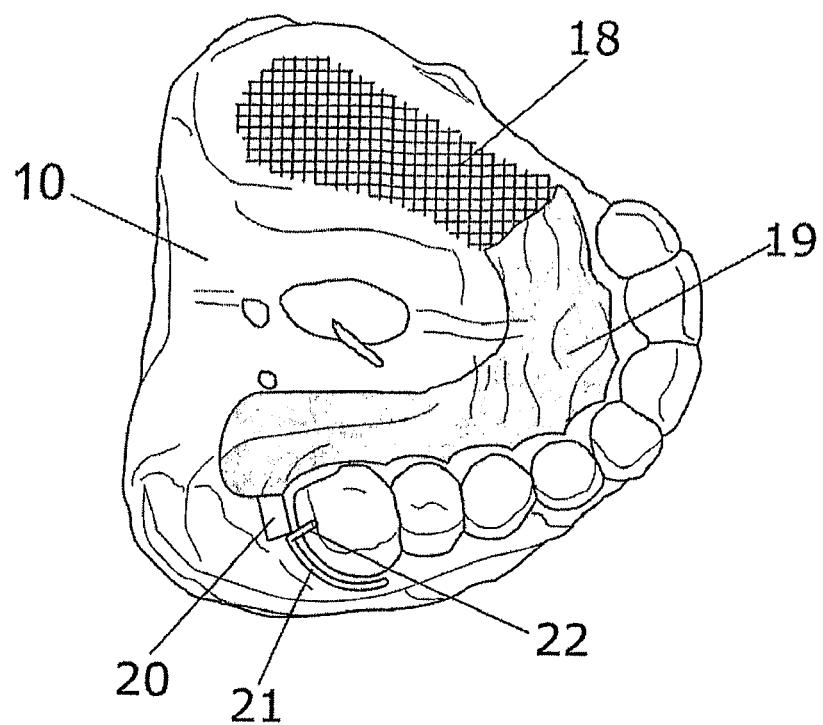
FIG. 6 shows the form adopted by a major connector and a lattice once designed and projected on the three-dimensional image of the mould.

FIGS. 2 and 6 show the different stages of digital design made on the digitalized figure of the mould (10). FIG. 2 shows the front view, the plan view, left profile and perspective view of the figure of the mould (10). It is possible to choose any view required.

Figure 3:
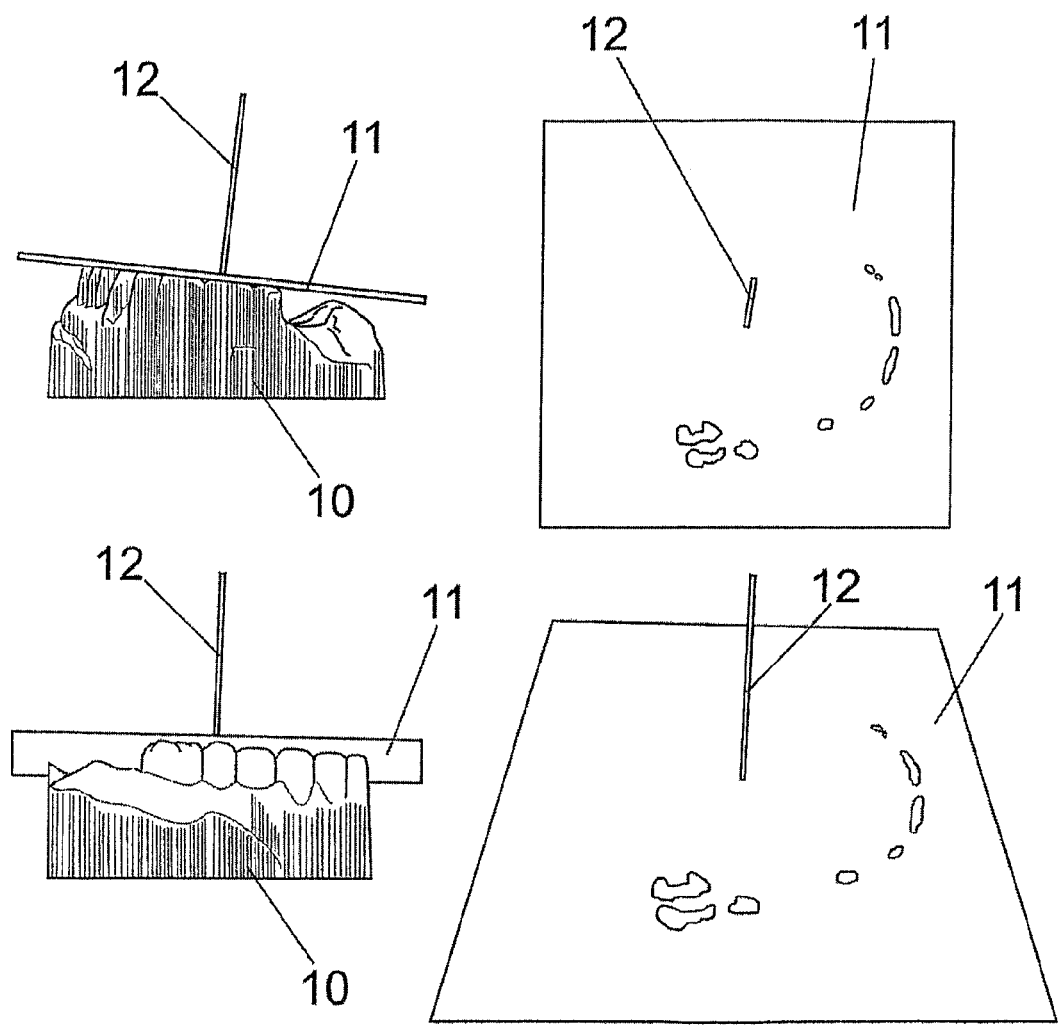
FIG. 3 shows the same previous representations on which a plane parallel to the palate and the corresponding insertion axis has been selected.

FIG. 3 shows the disposal of a plan (11) parallel to the palate and which aims to have the greatest number of intersections on the dental pieces at the same height. As a result of said plane (11) an insertion axis (12) is obtained, which will have a specified inclination.

Figure 4:
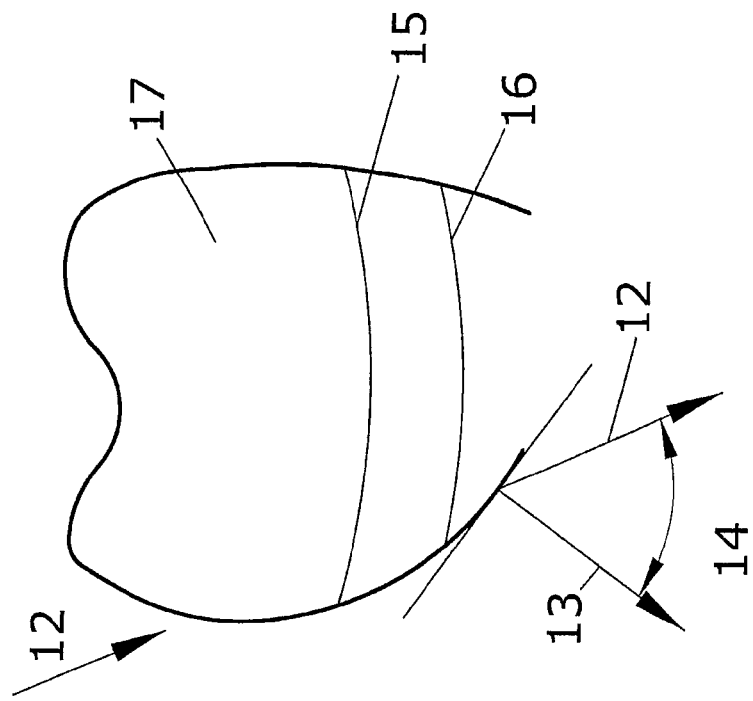
FIG. 4 shows a simplified representation of a dental piece whereon different retention points have been marked, and below, the previous dental piece has been represented whereon an equator line, as well as a possible paralleling line has been marked.
Figure 4:
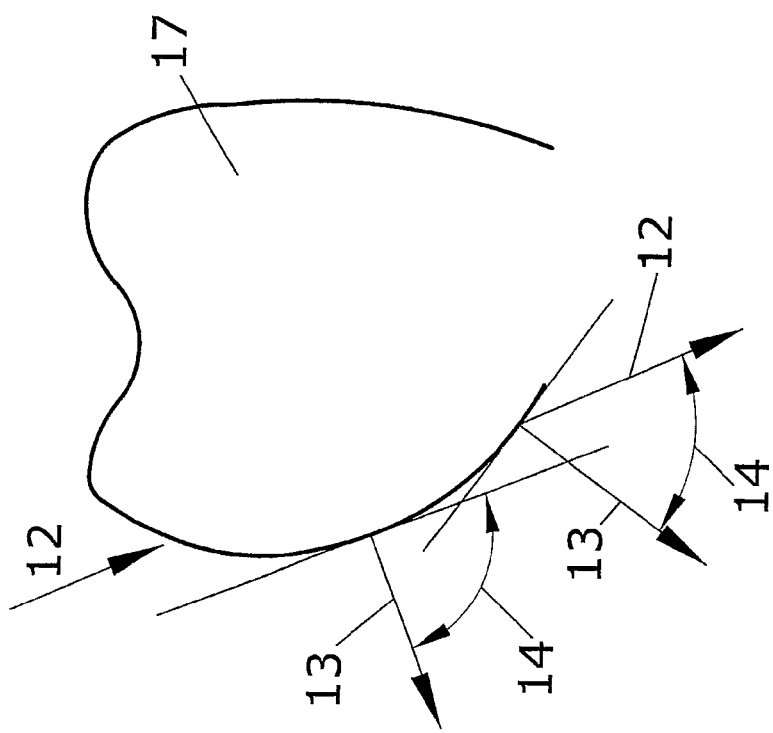

FIG. 4 shows how the different retentive areas can be displayed on a dental piece (17); for this purpose, indicator means are used to measure the angle (14) formed by the normal (13) to the tangent plane for each point of the dental piece with the insertion axis (12).

The retention angle (14) shown on the upper part is 90° or, in other words, the retention is minimal, whilst the retention angle shown on the lower part of the upper figure has a retention angle (14) smaller than 90°.

The figure to the right represents a line of the dental equator (15), which would represent the line of points of a minimal retention. Under said line (15), a paralleling line is represented (16) which as is shown, the insertion angle (14) which forms the normal to the tangent plane to the paralleling point with the insertion axis is less than 90° for which reason the retention is not minimal.

The indicator means used to indicate the retention angle can be various; for example, a colour scale or any other similar means.

Figure 5:
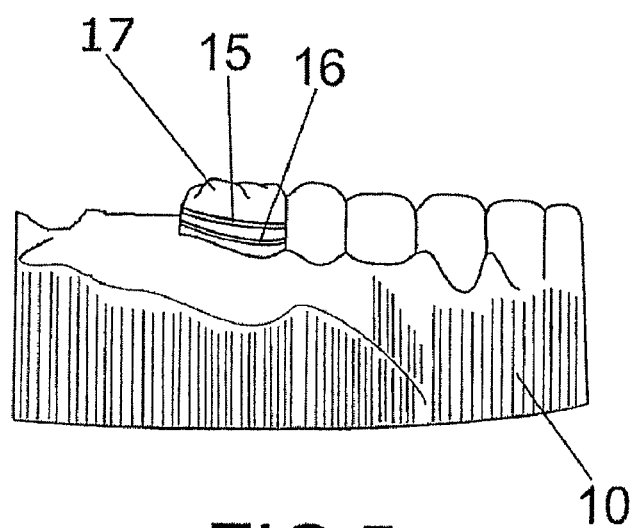
FIG. 5 shows a representation of the mould where an equator line of a dental piece is marked, and as well as a paralleling line under the dental equator.

FIG. 5 shows the dental equator (14) marked on the dental piece (17). The paralleling line (16) is represented under the line of the dental equator (14).

Therefore, the selection of the paralleling line (16) from the distance to the equator line (15) is a combination of practical securing and aesthetic factors.

FIG. 6 shows the disposal of the elements or components of the prosthesis once projected on the mould. Among the represented elements, we find a major connector (19), a lattice (18), a minor connector (20), a clamp (21) and a stop (22).

Other elements which can be used and have not been represented are the bristles and pearls, both used in the areas one wants to maximize, for example on the occlusal surfaces. These are designed for the time when the gripping material is filled.

The design process of the different elements, which form the removable dental prosthesis, will be made on the three-dimensional representation of the digitized mould.

The digitized mould is formed by a series of adjacent triangles, where each of the triangles is defined by their vertices and they are, in turn, defined by their co-ordinates (x, y, z); each of the vertices also has associated a normal, which is the mean of the normal of the sides or surfaces of the adjacent triangles to said vertices.

The lattices and connectors are designed on the screen where the three-dimensional representation of the digitized mould appears, defining a closed contour which is formed by a series or succession of points which will be marked inside the triangles which form the three-dimensional mould.

For the representation of the clamps, in first place the run or profile that they must follow or adopt is designed, a design which is made on the three-dimensional representation of the digitized mould, it being possible to choose the section of the clamp, and the form that we want the clamp to adopt both at the beginning and at the end from a library.

Figure 7:
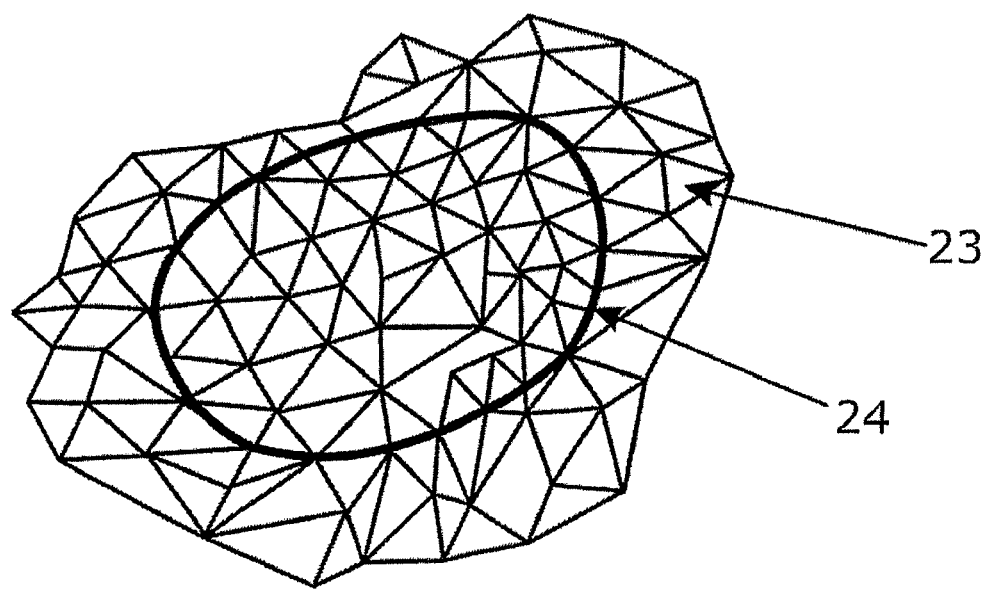
FIG. 7 shows a simplified representation of the surface of the digitized mould formed by a series of triangles on which a surface defined by a profile or contour has been designed in planar manner.

FIG. 7 shows an approximate representation of a digitized surface formed by a series of triangles (23) whereon a run or profile (24) has been defined, similar to that which could be defined on the design of the elements of the removable dental prosthesis. Said profile or run, in short, is a polygon resulting from joining the marked points on the triangles, which form the digitized mould.

With regard to the lingual bar, the run will also be marked, choosing the section and the form of the lingual bar from a library.

Therefore, all the elements of the removable prosthesis are formed by a succession of points defined by their three spatial co-ordinates, in addition to the parameters chosen as section, final form of the clamp, initial form of the clamp, web of the lattice, etc.

Once the basic form of the elements, which form the removable prosthesis, has been defined, we must extrude said elements in order to give them volume.

For clamps or lingual bars, the process as explained in the explanation of the invention, consists of:

A first stage of the flat part of the clamp or lingual bar, defined according to the marked profile or run, defining an upper and a lower band in relation to said profile, which are chosen according to the section of the desired clamp type.

Extrusion associating to each point of the profile or run the correspondent section according to the clamp type, generating a succession of sections disposed in continuous form.

For lattices or connectors, the extrusion process is as has already been explained. The lattice or the connector will be defined by a profile or a closed shape formed by a succession of points, which will be defined by their three co-ordinates. Each of the points of the closed profile or contour of the lattice or connector will be marked in the interior of a triangle which forms the digitized mould, proceeding to project the digitized mould as the points of the profile marked according to a plane whose normal is the mean of the normal of the triangles which contain the profile's points.

Figure 8:
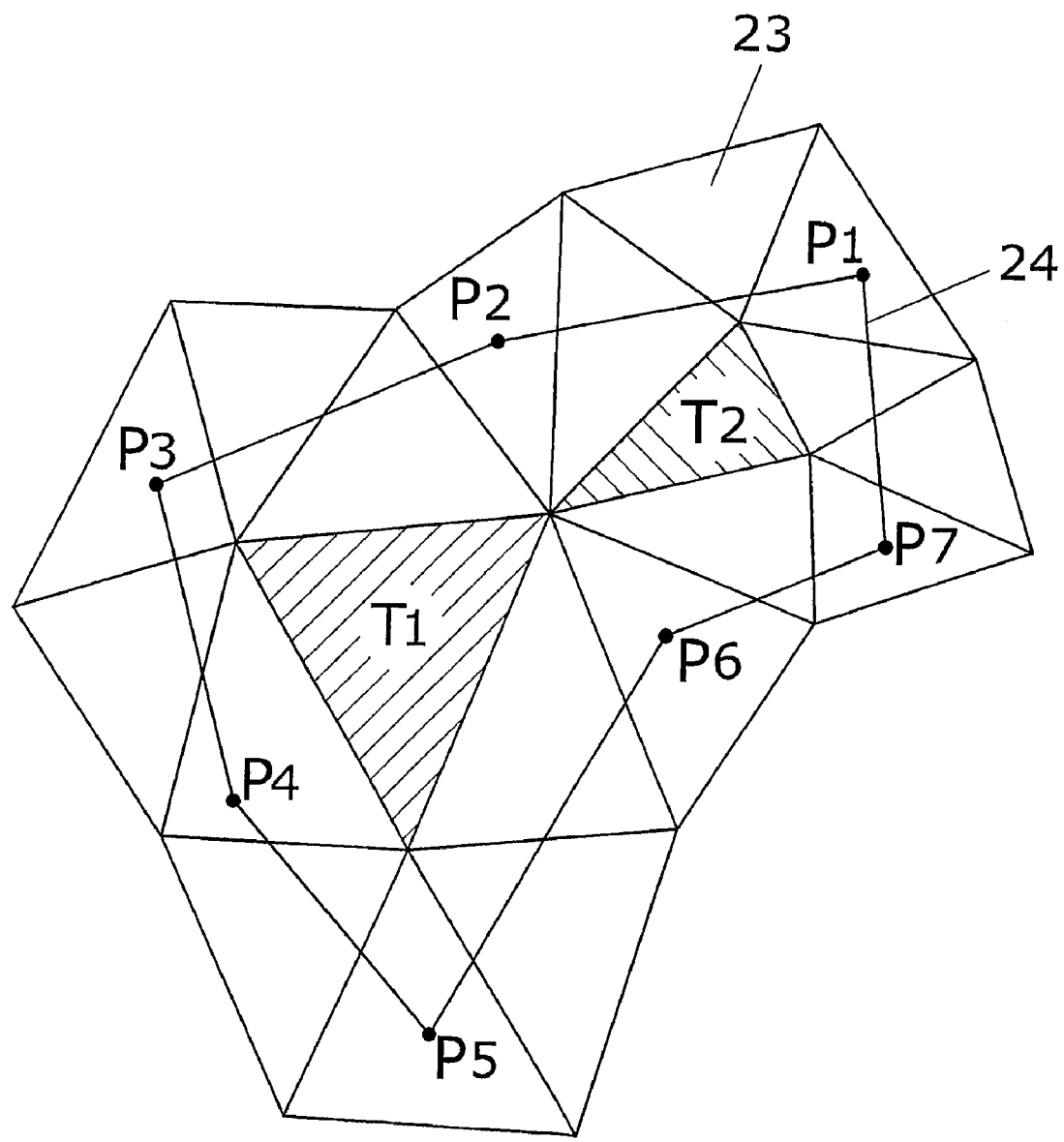
FIG. 8 shows a succession of triangles whereon a polygon resulting from the profile or contour defined on the triangles has been marked.
Figure 9:
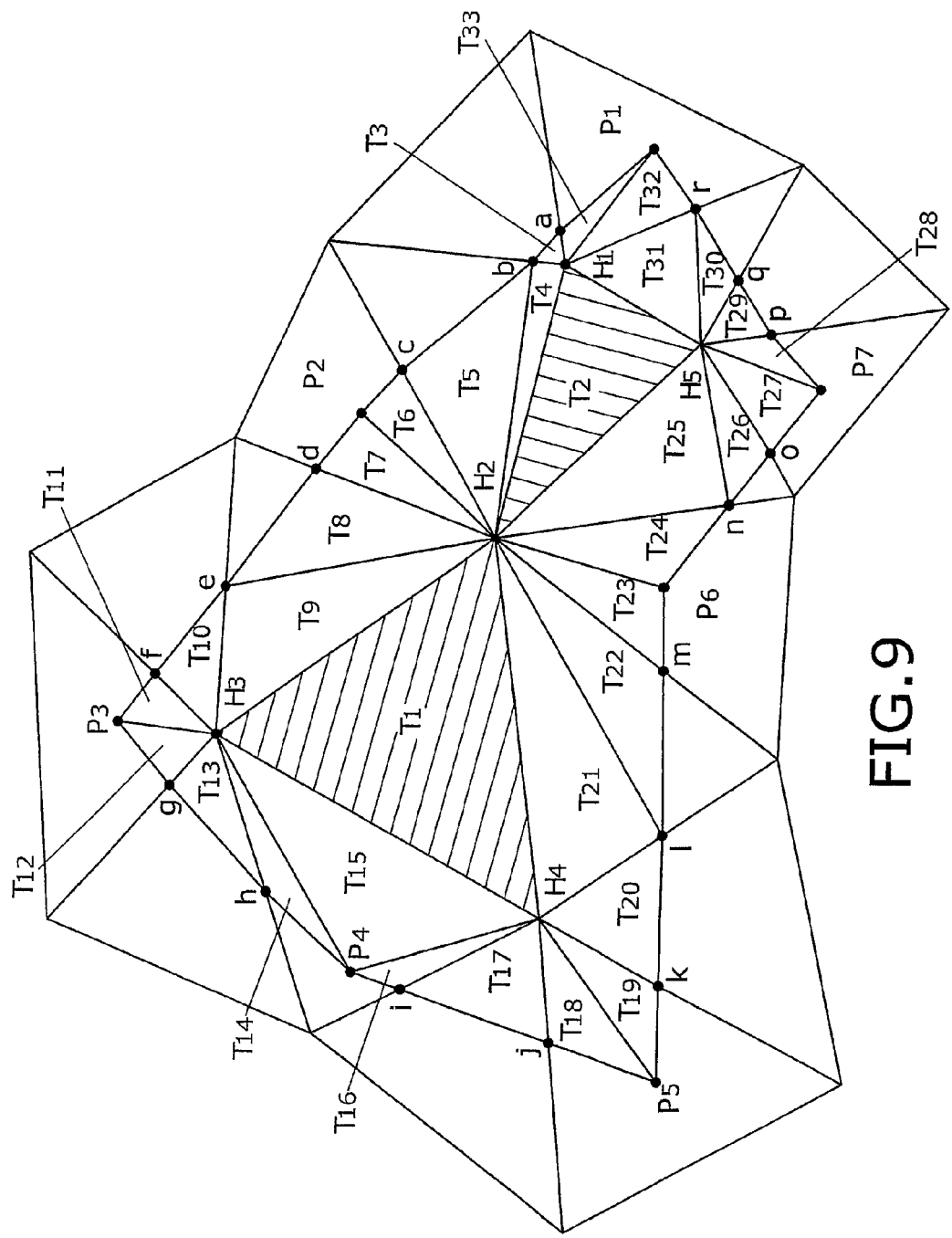
FIG. 9 shows how to produce the different triangles interior to the polygon formed on the profile or contour.

Next, we examine all the memory where the data is stored in relation to co-ordinates (p', v') of the projected triangles to ascertain:

the triangles of the mould, which are contained inside the traced polygon, i.e. those with vertices inside the polygon the triangles with one of their vertices inside the traced polygon the triangles with two of their vertices inside the polygon the triangles, which, although they have the three vertices outside the traced polygon are cut by said polygon FIG. 8 shows a partial and simplified representation of a succession of triangles (23), which are part of the digitized mould; it also represents a profile or run (24) formed by a succession of points P1-P7, which are marked inside the triangles.

The representation shown in this FIG. 8 would be the set of triangles projected according to the mean of the normal of the triangles which contain the points of the profile or run; the points of the profile or run would also be projected.

The triangles, which have all their vertices inside the traced polygon P1-P7, which corresponds to the design we want to give to the piece, are marked directly; in this case, it would be triangles T1 and T2, recovering their values before the projection.

In the case of the triangles with one of their vertices (H1-H5) inside the marked polygon, the cutting points of the polygon with the sides of the triangle are found and it is ascertained if there are or there are not any points of the polygon inside said triangle.

If there are no points of the polygon inside the triangle, for example, triangles T3, T10, T13, T17, T20, and T29 the obtained cutting points (a, b for T3), (e, g for T10), (g, h for T13), (i, j for T17), (k, l for T20), and (p, q for T29) and the vertex interior to the polygon (H1-H5) configures a new triangle which is part of the element.

If there are any points of the polygon contained in said triangle new triangles are formed, whose vertices are the vertex interior to the polygon, an obtained cutting point and the point of the polygon interior to the triangle. This way we have:

Triangle T6 formed by cutting point c, point of the polygon P2 and interior vertex H2

Triangle T7 formed by cutting point d, point of the polygon P2 and interior vertex H2.

Triangle T11 formed by cutting point f, point of the polygon P3 and interior vertex H3.

Triangle T12 formed by cutting point g, point of the polygon P3 and interior vertex H3.

Triangle T18 formed by cutting point j, point of the polygon P5 and interior vertex H4.

Triangle T19 formed by cutting point k, point of the polygon P5 and interior vertex H4.

Triangle T23 formed by cutting point m, point of the polygon P6 and interior vertex H2

Triangle T24 formed by cutting point n, point of the polygon P6 and interior vertex H2.

Triangle T27 formed by cutting point o, point of the polygon P7 and interior vertex H5.

Triangle T28 formed by cutting point p, point of the polygon P7 and interior vertex H5

Triangle T32 formed by cutting point r, point of the polygon P1 and interior vertex H1.

Triangle T33 formed by cutting point a, point of the polygon P2 and interior vertex H1.

If the triangles have two of their vertices inside the marked polygon, the cutting points are found and it is ascertained if there is any point of the polygon contained in said triangle, having two possible situations:

if there is no points of the polygon contained inside said triangle two new triangles are formed whose vertices are: one of the triangles with two vertices of the new triangles interior to the polygon and one of the cutting points, and the another triangle is formed by the two cutting points and as a third vertex one of the vertices of the triangles interior to the polygon.

This way we would have the following triangles:

Triangle T4 formed by H1, H2 and by cutting point b

Triangle T5 formed by cutting points b and c and by interior vertex H2.

Triangle T8 formed by cutting points d and e and by interior vertex H2

The triangle T9 formed by interior vertices H1 and H2 and by cutting point e.

Triangle T21 formed by vertices H2 and H4 and by cutting point 1.

Triangle T22 formed by cutting points l and m and by interior vertex H2

Triangle T25 formed by interior vertices H2 and H5 and by cutting point n.

Triangle T26 formed by interior vertex H5 and by cutting points n and o.

Triangle T30 formed by interior vertex H5 and by cutting points q and r.

Triangle T31 formed by interior vertices H1 and H5 and by cutting point r.

if there is any point of the polygon interior to the triangle that has two vertices inside the polygon, three triangles are formed whose vertices are:

The interior point, one of the cutting points and one of the interior vertices.

The interior point and the two interior vertices

The interior point, the other cutting point, and the interior point not used in case 1.

In this case, the new triangles that are generated would be T14, T15 and T16 since there is a point P4 of the polygon interior to a triangle with two interior vertices H3 and H4.

this way Triangle T14 is formed by H3, cutting point h and point of the polygon P4 this way Triangle T15 is formed by H3 and H4 and point of the polygon P4 this way the triangle is formed by H4, cutting point i, and point of the polygon P4

In the last case, which is the one represented in FIG. 10, to ascertain those triangles which have no any vertex inside the space defined by the designed polygon, and that part of its surface could form the interior part to the polygon, we proceed as follows:

It is examined triangle by triangle, making a first selection where those triangles are rejected, which are impossible to be cut by the traced polygon From among those triangles which could be cut by the polygon. First, we calculate the segments, which join the vertices of the triangles, and it is checked that none of said segments is cut by one of the multiple straight portions, which compose the polygon.

If there appears any cutting points, the points of the polygon included between the cutting points found on the segments of the triangles are ascertained, forming new triangles which have as vertices the cutting points found and the points of the polygon that are inside the triangle whose one side cuts the polygon.

Figure 10:
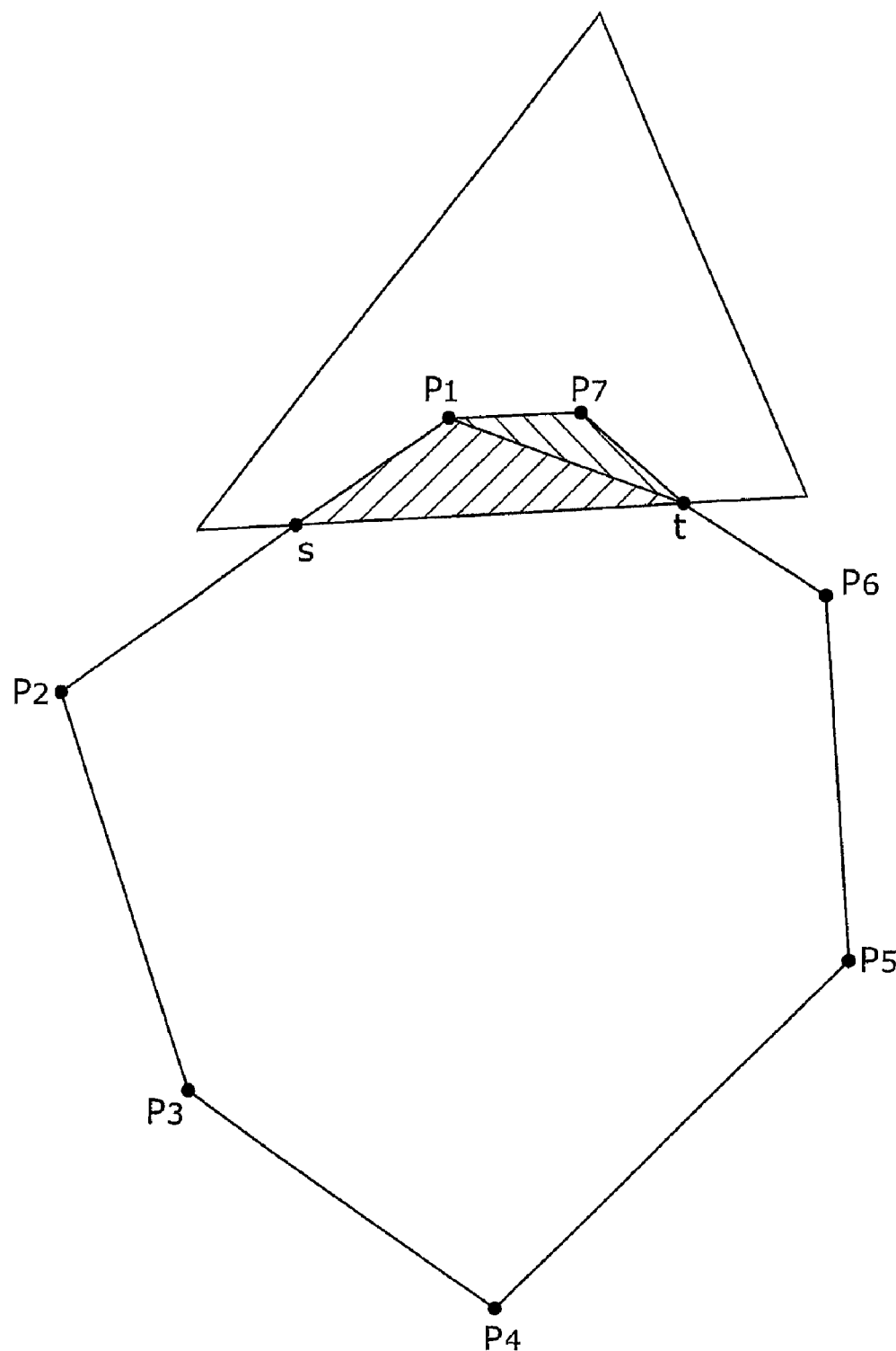
FIG. 10 shows, in simplified form, the case of a triangle which having no vertices in the interior space of the polygon it cuts it nevertheless.

Thus, in FIG. 10, of the newly found triangles, one of them will have as vertices cutting points s and t and one of the points of the polygon interior to the triangle which has no vertex interior to the polygon, whilst the other one will have as vertices P1 and P7 and one of the found cutting points.

Therefore, a triangulation process has been performed of the interior surface of the polygon which forms the profile or run once the whole set has been projected according to the direction of the previously defined normal.

Since all the triangles which form the digitized model are defined by their vertices and each of those by their three co-ordinates, as well as by a normal which is the mean of the normal of the surfaces of the adjacent triangles.

In the newly obtained triangles which form part of the interior of the polygon with one or two of their vertices inside the polygon, or having part of their surfaces without any vertices inside the polygon, the three-dimensional data of the known data is recovered, whilst the newly obtained vertices, which are basically the cutting points with the polygon and they have co-ordinates (p', v') they are transformed to their three-dimensional co-ordinates (x, y, z) taking in consideration the projection made according to the obtained normal.

In other words, we finally obtain a closed profile or contour formed by triangles, all of them interior and they are defined by their vertices and them by their three-dimensional co-ordinates.

Next, since the total projection of the digitized model has been made, we identify the surfaces, which share at least one edge, generating at least two different surfaces.

Then, we choose the surface we are interested in and which will be the surface that is the nearest to the defined profile or contour, which will in fact have zero distance in most of its points.

Next all points of the selected surface are extruded or elevated in the normal direction of each point, as we have said the normal of each point is the mean of the normal of the surfaces of the adjacent triangles.

Then, a Gauss filter is used to smooth the edges applying it on all the sides except on those, which are in contact with the palate, applying it to all of the elements that form the removable denture.

Next, the file should be prepared for its manufacturing, and the following should be done:

first, perform a process of joining the different elements that form the designed removable prosthesis eliminating the superpositions between the pieces. This process is known as "voxel", and for this purpose it is identified if the interior is part of the defined volume, using a double beam technique the voxel identified first by the one which is entering and the latter by the one which is exiting, so that we obtain a volume defined by its external shape and managing to eliminate all superpositions of the design elements. The definition of the voxelization must be greater, or at least equal to, that of the machine, or in other words, the edge of the cube or voxel must be smaller than or equal to the resolution distance of the machine.

Finally, a conversion process is performed from a compact volume to a closed continuous and connected 3D surface.

If necessary, smoothing filters can be used.

Variations in materials, the form, the size and disposal of the component elements, described in a no limitative mode, do not alter the essential nature of the invention, this being sufficient for it to be reproduced by a person skilled in the art.

The invention claimed is:

1. A manufacturing process of digitally designed removable dental prostheses, wherein a digital relief process is performed in areas where a lattice would be placed, comprising the following steps:
   A) scanning a mould produced from an impression taken of a patient's mouth, said scanning generating a digitized mould;
   B) transmitting a file produced by said scanning to a computer where a design is performed, said file containing a first three-dimensional representation of said digitized mould;
   C) digitally designing pieces and components of a removable dental prosthesis, making a digital design of said pieces and components on a representation of said digitized mould;
   D) giving thickness to said digital design of said pieces and components;
   E) producing and transmitting said file to a manufacturing equipment of metal pieces by means of sintered powder whereto a high-energy ray is applied after performing said digital design of said removable dental prosthesis;
   F) digitally calculating an insertion axis;
   G) digitally paralleling said removable dental prosthesis, said digitally designing pieces and components of said removable dental prosthesis comprises using a major connector, a minor connector, a lattice, a stop, a clamp, a lingual bar, a bristle and pearls;
   H) extruding said pieces and components;
   I) smoothing sharp edges of said pieces and components;
   J) eliminating a superposition of said pieces and components; and
   K) converting a closed continuous and connected surface to a three-dimensional representation, further characterized in that a plane is disposed parallel to a palate when said digitally calculating said insertion axis, said palate has a greatest number of insertions on said removable dental prosthesis at a same height, said insertion axis is perpendicular to said plane.

2. The manufacturing process of digitally designed removable dental prostheses according to claim 1, further characterized in that said digitally paralleling said removable dental prosthesis, comprises the following step:
   M) producing a perimeter line of said pieces and components produced from a retention degree indication for each said pieces and components.

3. The manufacturing process of digitally designed removable dental prostheses according to claim 2, further characterized in that said retention degree is obtained according to an angle, which forms a normal of said plane to a point of said removable dental prosthesis with said insertion axis.

4. The manufacturing process of digitally designed removable dental prostheses according to claim 2, further characterized in that said retention degree indication offered by said point of said removable dental prosthesis is indicated by means of a color scale.

5. The manufacturing process of digitally designed removable dental prostheses according to claim 2, further characterized in that lattices and connectors are designed on said three-dimensional representation of said digitized mould defining a profile, previously choosing said thickness from a library of possible options.

6. The manufacturing process of digitally designed removable dental prostheses according to claim 2, further characterized in that clamps and lingual bars are designed on said three-dimensional representation of said digitized mould defining a profile, choosing for said clamps their section, as well as a form that said clamp will adopt at its ends, and with regard to said lingual bars, their respective section and form are chosen.

7. The manufacturing process of digitally designed removable dental prostheses according to claim 2, further characterized in that an extrusion of said clamps and said lingual bars comprises the following steps:
   N) defining a flat part of said clamp and said lingual bars from said profile, marked on said digitized mould, whereby an upper and lower band are defined related to said profile;
   O) extruding each point of said profile to generate a succession of sections continuously disposed, which form said clamp and said lingual bars with their definitive form.

8. The manufacturing process of digitally designed removable dental prostheses according to claim 7, further characterized in that said extrusion of said lattices and connectors comprises the following steps:
   P) calculating an arithmetic average of a normal of triangles that contain said points of said profile of said lattices and connectors to obtain an approximated projection direction;
   Q) projecting said digitalized mould on said plane, going from three co-ordinates (x, y, z) to two co-ordinates (p', v');
   R) projecting points which form said profile of said lattices and connectors on said plane;
   S) joining said points by a polygon, said polygon forms said profile of said lattices and connectors, ascertaining which of projected said points is outside or inside of a contour;
   T) examining memory where data is related to said two co-ordinates (p', v') of said projected points was stored to ascertain:
   a) said points of said digitized mould, which are contained within said traced polygon;
   b) said points, which have one of their vertices inside said traced polygon;
   c) said points, which have two of their vertices inside said traced polygon;
   d) said points, which even having their three vertices outside said traced polygon, are cut by said traced polygon;

U) recovering three-dimensional values of known data and of newly found said points, transforming said two co-ordinates (p', v') into said three-dimensional co-ordinates (x, y, z);

V) Identifying surfaces, which share at least one edge;

W) selecting of the surface, which is the nearest to said defined profile or contour; and X) extruding all said points of selected said surfaces in said direction of said arithmetic average of said normal of said triangle of each said point.

9. The manufacturing process of digitally designed removable dental prostheses according to claim 8, further characterized in that values are identified when said triangles have all their vertices inside said traced polygon before projection.

10. The manufacturing process of digitally designed removable dental prostheses according to claim 9, further characterized in that when said triangles have all their vertices inside said traced polygon cutting points are found of said polygon with said sides of said triangle, if there is no point of said polygon inside said triangle, said cutting points obtained and the interior vertex to said polygon configure a new triangle, and if there are any said point of said polygon contained in said triangle, new triangles are formed, which vertices are the interior vertices to said polygon, a cutting point obtained and said point of said polygon interior to said triangle.

11. The manufacturing process of digitally designed removable dental prostheses according to claim 9, further characterized in that if said triangles having two of their vertices inside said traced polygon, said cutting points are found and it is ascertained if there is any point of said polygon contained in said triangle, if there is no any point of said polygon contained inside said triangle, two new triangles are formed, which vertices are one triangle with two vertices of said triangle interior to said polygon and one of said cutting points, and another triangle is formed by said two cutting points and, as a third vertex, one of the vertices of said triangle interior to said polygon, if there is any point of said polygon interior to said triangle, which has two of its vertices inside said polygon, three new triangles are formed, which vertices are its interior point, one of said cutting points and one of said interior vertices, its point of interior and two interior vertices, and its interior point, the other cutting point, and the interior vertex, not used in said first case.

12. The manufacturing process of digitally designed removable dental prostheses according to claim 9, further characterized in that to ascertain said triangles which have three vertices outside said traced polygon, each of said triangles is examined, making a first selection where said triangles, which are impossible to be cut by the traced polygon are rejected, from among said triangles, which could be cut by the polygon, first, segments that join said vertices of said triangles are calculated, and it is checked that none of said segments is cut by one of multiple straight lines, which compose said polygon; and if there appears any of said cutting points, said points of said polygon included between said cutting points found on the segments of said triangles are ascertained, forming new triangles which have as said vertices said cutting points found and said points of said polygon that are inside said triangle having one side that cuts said polygon.

13. The manufacturing process of digitally designed removable dental prostheses according to claim 1, further characterized in that said smoothing of said sharp edges is performed using a Gauss filter, applying it to all of elements of said removable dental prosthesis.

14. The manufacturing process of digitally designed removable dental prostheses according to claim 1, characterized in that an elimination of a superposition of different elements designed is realized by a double beam technique identifying a first voxel as the one on which enters said double beam, and a last voxel whereby said double beam exits, where the definition of said first and last voxel must be greater than or equal to a resolution distance of a manufacturing equipment of said removable dental prosthesis.

15. The manufacturing process of digitally designed removable dental prostheses according to claim 8, further comprising the steps of:

Y) producing scanner equipment of said moulds after said impression is taken from the patient's mouth;

Z) manufacturing equipment of said metal pieces by means of said sintered powder applying a high-energy ray;

AA) digitally generating said removable dental prostheses.

16. The manufacturing process of digitally designed removable dental prostheses according to claim 15, which has means necessary to perform a digital relief of said digitized mould, to digitally calculate said insertion axis, to digitally perform said paralleling of said removable dental prostheses, to digitally design on said three-dimensional representation of said digitized mould a geometry and said disposition of said elements and components of said removable dental prostheses with said major connector, said minor connector, said stop, said lattice, said clamp, said bristle, said pearls, said lingual bars, means to extrude said removable dental prostheses previously designed forming said closed continuous and connected surface in said three-dimensional one.

17. The manufacturing process of digitally designed removable dental prostheses according to claim 16, further comprising digital support to contain necessary programme for said digital designing of the removable dental prostheses.

* * * * *